United States Patent [19]

Tokitoh et al.

[11] Patent Number: 5,118,885
[45] Date of Patent: Jun. 2, 1992

[54] PROCESS FOR PRODUCING OCTA-2,7-DIEN-1-OL

[75] Inventors: Yasuo Tokitoh, Ibaragi; Tamio Higashi, Chiba; Kenichi Hino, Funabashi; Masami Murasawa, Ibaragi; Noriaki Yoshimura, Kurashiki, all of Japan

[73] Assignee: Kuraray Co., Ltd., Kurasahiki, Japan

[21] Appl. No.: 634,514

[22] Filed: Dec. 27, 1990

[30] Foreign Application Priority Data

Dec. 30, 1989 [JP] Japan .................................. 1-341691

[51] Int. Cl.$^5$ ...................... C07C 29/36; C07C 29/44; C07C 33/02
[52] U.S. Cl. .................................................. 568/909.5
[58] Field of Search ..................................... 568/909.5

[56] References Cited

U.S. PATENT DOCUMENTS

| 3,670,032 | 6/1972 | Romanelli | 568/909.5 |
| 4,356,333 | 10/1982 | Yoshimura | 568/840 |
| 4,417,079 | 11/1983 | Yoshimura | 568/903 |
| 4,962,243 | 10/1990 | Roeper | 568/909.5 |

Primary Examiner—Marianne Cintins
Assistant Examiner—Rebecca Cook
Attorney, Agent, or Firm—Oblon, Spivak, McClelland, Maier & Neustadt

[57] ABSTRACT

An improved process for producing octa-2,7-dien-1-ol which comprises reacting butadiene with water in an aqueous sulfolane solution containing a carbonate and/or bicarbonate of a monodentate tertiary amine in the presence of a palladium compound and a phosphonium salt.

9 Claims, No Drawings

PROCESS FOR PRODUCING OCTA-2,7-DIEN-1-OL

BACKGROUND OF THE INVENTION

1. Field of the Invention

The present invention relates to an improved process for producing octa-2,7-dien-1-ol by reacting butadiene with water.

2. Description of the Prior Art

Synthesis of octa-2,7-dien-1-ol by reacting butadiene with water in the presence of a palladium catalyst is known. Since, as is well known, palladium catalysts are very expensive noble metal catalysts, it is important for the purpose of commercially producing octa-2,7-dien-1-ol at a low cost and on a large scale, to solve the following technical problems 1) through 4).

1) to achieve a high reaction rate at a commercially permissible palladium catalyst concentration (several milligram atoms as palladium atom per 1 liter of reaction mixture);

2) to assure a sufficiently high selectively to octa-2,7-dien-1-ol;

3) to allow the activity of the palladium catalyst to be maintained stably over a long period of time; and 4) to assure that the product octa-2,7-dien-1-ol can be efficiently separated from the reaction mixture without entailing a deactivation of the palladium catalyst.

While octa-2,7-dien-1-ol is generally separated by distilling the reaction mixture containing the palladium catalyst, a detailed study by the present inventors revealed that when the distillation temperature exceeds about 120° C., the palladium catalyst tends to be decomposed to the metal and inactivated.

As a process that would solve the above technical problems, two inventors including one of the present inventors have already proposed the following production process (see U.S. Pat. Nos. 4,356,333 and No. 4,417,079), which comprises:

(I) reacting butadiene with water in an aqueous sulfolane solution containing a carbonate and/or bicarbonate of a monodentate tertiary amine having a basicity constant (pKa) of at least 7 in the presence of a palladium compound and a hydrophilic monodentate phosphine in an amount of at least 6 moles per 1 gram atom of the palladium, to synthesize octa-2,7-dien-1-ol, (II) separating the product octa-2,7-dien-1-ol by extracting at least part of the reaction mixture obtained in step (I) with a saturated aliphatic hydrocarbon, a mono-olefinic hydrocarbon or an alicyclic hydrocarbon, and (III) recycling at least part of the extraction residue containing the catalyst components as obtained in step (II) to step (I).

According to the process described in U.S. Pat. Nos. 4,356,333 and 4,417,079, octa-2,7-dien-1-ol can be produced at high reaction rate and selectivity even when a palladium catalyst is present in a low concentration and, in addition, can be separated from the reaction mixture without entailing a deactivation of the palladium catalyst, thus permitting re-use of the palladium catalyst by recycling. However, it has been found that even with this process there still remains, when a long-term continuous operation is conducted on commercial scale, the following problems to be solved. There are eluted, although in extremely small amounts, catalyst components such as palladium, phosphorus compound, tertiary amine and sulfolane, into the extract obtained upon separation of octa-2,7-dien-1-ol from the reaction mixture. When this extract is subjected to distillation as it is to separate unreacted butadiene, the extracting solvent used and catalyst components from octa-2,7-dien-1-ol, most of the eluted palladium catalyst precipitates as metal in the waste, whereby the reboiler used decreases its thermal efficiency with time to render the separation by distillation difficult to continue and the amount of by-produced high boiling substances increases. U.S. Pat. No. 4,356,333 also describes that trace amounts of catalyst and phosphine contained in the extract can be removed by washing the extract with for example an aqueous sulfolane solution prior to separation treatment of octa-2,7-dien-1-ol from the extract. According to the study made by the present inventors, however, the recovery rate of palladium catalyst from the extract in this process is 30 to 40% at most, and it is difficult, by simply improving the apparatus used to achieve high washing efficiency, to recover the palladium catalyst from the extract to such an extent as to suppress the decrease in thermal efficiency of reboiler and generation of high boiling by-products. Furthermore, the palladium compound and phosphorus compound recovered by this distillation have changed to forms that no longer have catalyst activity as they are and, hence, require to be retreated in some manner. A process requiring such retreatment cannot be said to be economical. It is needless to say that, where such compounds as n-octanol are produced at a comparatively low price and commercially in large amount, serious problems will arise from even a few percentages of: a) increase in elution of palladium catalyst into the extract, b) decrease in recovery rate of the catalyst component, c) increase in by-production of high-boiling compounds, d) decrease in the thermal efficiency of reboiler, and the like.

Accordingly, a principal object of the present invention is to provide a process for producing octa-2,7-dien-1-ol that is free from the above problems.

This object as well as other objects and advantages of the present invention will become apparent to those skilled in the art from the following detailed description.

SUMMARY OF THE INVENTION

As a result of intensive study to develop a process for producing octa-2,7-dien-1-ol that will be free from the above problems, the present inventors have found that washing an extract containing octa-2,7-dien-1-ol with an aqueous sulfolane solution in the presence of a water-soluble phosphine assures an efficient recovery of palladium catalyst and phosphorus compounds that maintain catalyst activity from the extract, and completed the invention.

Thus, the present invention provides a process for producing octa-2,7-dien-1-ol, which comprises:

(1) reacting butadiene with water in an aqueous sulfolane solution containing a carbonate and/or bicarbonate of an monodentate tertiary amine having a basicity constant (pKa) of at least 7 in the presence of a palladium compound and a phosphonium salt, while maintaining the mole ratio of butadiene to octa-2,7-dien-1-ol at at least 0.6, to synthesize octa-2,7-dien-1-ol;

(2) separating octa-2,7-dien-1-ol by extracting at least part of the reaction mixture obtained in step (1) with a saturated aliphatic hydrocarbon, a mono-olefinic hydrocarbon or an alicyclic hydrocarbon;

(3) feeding at least part of the extraction residue containing the catalyst components as obtained in step (2) to the synthesis reaction step (1) of octa-2,7-dien-1-ol;

(4) washing the extract containing octa-2,7-dien-1-ol as obtained in step (2) with an aqueous sulfolane solution in the presence of a water-soluble phosphine and separating the mixture into the aqueous sulfolane solution layer and the washed extract layer;

(5) feeding at least part of the aqueous sulfolane solution layer obtained in step (4) to the extraction step (2); and (6) distilling the washed extract layer obtained in step (4).

DESCRIPTION OF THE PREFERRED EMBODIMENTS

It is preferred that the water-soluble phosphine used in step (4) in the present invention to be present when the extract containing octa-2,7-dien-1-ol as obtained in step (2) is washed with an aqueous sulfane solution be one represented by the following formula (I)

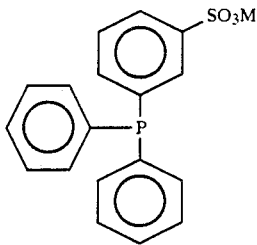

wherein M represents an alkali metal. Examples of the alkali metal represented by M in the formula (I) are lithium, sodium and potassium. The water-soluble phosphine is suitably used in an amount of at least 1 mole per gram atom of palladium contained in the extract obtained in step (2). In the absence of the water-soluble phosphine, only about 30 to 40% of the palladium catalyst contained in the extract obtained in step (2) can be recovered into the aqueous sulfolane solution. The presence of the water-soluble phosphine in an amount of at least 1 mole per gram atom of palladium contained in the extract obtained in step (2) can assure recovery of 90 to 100% of the palladium catalyst into the aqueous sulfolane solution. Moreover, at this time, the amount of phosphorus compounds eluted into the extract containing octa-2,7-dien-1-ol never increases. There is no particular upper limit with respect to the amount of the water-soluble phosphine to be used, and the amount preferably corresponds to that contained in the washed extract obtained in step (4), i.e. an molar equivalent of the phosphorus compound being eluted from the reaction system. As the aqueous sulfolane solution used in step (4) preferably used is at least part of the aqueous sulfolane solution recovered from the waste obtained in step (6). In this case, the amount of water used is preferably not more than the total amount of water consumed by the reaction in step (1) and water eluted into the extract layer in step (4). It is suitable to conduct the washing in step (4) under an atmosphere of carbon dioxide. The partial pressure of carbon dioxide is preferably higher than 3 absolute pressures and lower than 20 absolute pressures, more preferably 4 to 16 absolute pressures. While the carbon dioxide pressure little influences the recovery rate of palladium catalyst and phosphorus compound into the aqueous sulfolane solution, it largely affects the recovery rate of the tertiary amine used. The recovery rate of the tertiary amine increases with the carbon dioxide pressure, and reaches 100% when the carbon dioxide pressure is 20 absolute pressures or above. The carbon dioxide partial pressure in step (4), however, need not be so high, since the tertiary amine can also be recovered efficiently, together with the extracting solvent, by distillation in step (6).

The washing is preferably conducted at 0° to 80° C., more preferably at 5° to 30° C., for the purpose of recovering the palladium catalyst with its activity well maintained. Washing at a temperature higher than 80° C. will cause not only the activity of the recovered palladium catalyst to decrease, but also the recovery rate of the tertiary amine to decrease. On the other hand, with washing at lower than 0° C., the washing solution layer and the washed extract layer become difficult to separate from each other. The washing may be conducted either continuously or batch-wise, and generally by using a conventional extracting and washing apparatus.

In step (6) in the present invention, that distills the extract washed in step (4), it is preferred to add dimethylglyoxime to the extract prior to the start of the distillation. The addition of dimethylglyoxime is effective for suppressing metallization of the palladium catalyst in the waste. The amount of dimethylglyoxime added is preferably at least 10 moles per gram atom of the palladium dissolved in the washed extract. Where the palladium catalyst has effectively been recovered in step (4), dimethylglyoxime is not necessarily added to the washed extract when said extract is distilled. Recovery of the palladium catalyst in step (4) and stabilization thereof by addition of dimethylglyoxime during distillation can suppress the metallization of the palladium catalyst in the waste, whereby stable distillation operation is assured.

In the process of the present invention, sulfolane is recovered from the waste obtained by distilling off octa-2,7-dien-1-ol in step (6).

The waste contains, besides sulfolane, high boiling substances such as dioctadienyl ether and lactones having 9 carbon atoms (hereinafter referred to as "C9 lactone") that are byproducts of the reaction. These byproducts form an azeotropic mixture with sulfolane. The azeotropic mixture phase-separates at about room temperature and forms a lower layer containing principally sulfolane. Although the selective separatability between sulfolane and the above high boiling substances are not high, sulfolane can be recovered in a rate of at least 90% when the waste or the liquid obtained by evaporating the waste is washed with water. The amount of water used for this purpose is preferably 0.2 to 1 time by weight of the total weight of water consumed in the reaction in step (1) and water eluted into the extract layer in step (4). With the amount of this water being less than 0.2 time that of the total weight of water consumed and eluted, the recovery rate of sulfolane decreases. On the other hand, if the amount exceeds 1 time that of the above total weight, it becomes necessary to distil off the exceeding amount of water by heat operation, and at this time high boiling substances such as C9 lactone contained in the aqueous sulfolane solution will hydrolyze to form unsaturated carboxylic acids having 9 carbon atoms. Where the aqueous sulfolane solution containing these unsaturated carboxylic acids having 9 carbon atoms is used as the washing solution in step (4), the unsaturated carboxylic acids remain in the aqueous sulfolane solution layer obtained in step (4), and then migrate into the extraction residue obtained in step (2) with which they will then be circulated to the synthesis reaction step (1) of octa-2,7-dien-1-ol. Since unsaturated carboxylic acids temporarily suppress the activity of palladium catalysts, an increase in the concentration of the carboxylic acids in the catalyst system in steady state is not preferred. From the above, it is preferred that the temperature of the water washing be around room temperature, and further that the residence time during the water washing be not extremely longer than the time required for phase separation. It is still more preferred to use hexane when recovering sulfolane from the waste or the liquid obtained by evaporation of the waste. Addition of hexane to the waste or the liquid obtained by evaporation of the waste permits recovery of sulfolane in a rate of at least 98%. In this case, generation of unsaturated carboxylic acids having 9 carbon atoms can be suppressed because water is not used. The use of hexane in combination with water is also possible for the purpose of recovering sulfolane. The washing may be conducted either batchwise or continuously, and generally by using a conventional extracting and washing apparatus.

In step (1) in the present invention, octa-2,7-dien-1-ol can be obtained by reacting butadiene with water in an aqueous sulfolane solution containing a carbonate and/or bicarbonate of an monodentate tertiary amine having a basicity constant (pKa) of at least 7 in the presence of a palladium compound and a phosphonium salt, while maintaining the mole ratio of butadiene to octa-2,7-dien-1-ol at least 0.6. The mole ratio of butadiene to octa-2,7-dien-1-ol must be maintained at 0.6 or higher, and is preferably 0.8 to 1.6. If the mole ratio of butadiene to octa-2,7-dien-1-ol decreases to less than 0.6, there will occur problems including: accumulation of insoluble polymers in the reaction mixture, deactivation of the palladium catalyst, decrease in the rate and selectivity of the reaction, and increase in the amount of the palladium catalyst eluted into the extract upon separation of octa-2,7-dien-1-ol. The mole ratio has no particular upper limit, and it is generally preferred to be not more than 2.0. Where the mole ratio exceeds 2.0, the total system becomes economically disadvantageous; since the amount of butadiene to be recovered increases, the reaction mixture becomes heterogeneous, whereby in the extraction procedure conducted succeeding the synthesis reaction of octa-2,7-dien-1-ol the amounts of sulfolane and others eluted into extract increase, and the system requires a large reaction vessel.

The butadiene used in the invention can be any of ones of the polymerization grade and chemical-reaction grade that are commercially available and one that is generally called "C4 fraction" in petrochemical industry and is a mixture of hydrocarbons. It is however preferred, in view of reaction rate and readiness of recovery of unreacted butadiene, to use butadiene of polymerization grade or chemical reaction grade.

The carbonate and/or bicarbonate of a monodentate tertiary amine having a basicity constant (pKa) of at least 7 used in step (1) in the present invention has functions of markedly enhancing the reaction rate while maintaining the selectivity to octa-2,7-dien-1-ol at a high level, stabilizing the activity of palladium catalyst and increasing the extraction yield of octa-2,7-dien-1-ol in extraction step (2) succeeding this step (1). Examples of the monodentate tertiary amine are trimethylamine, triethylamine, tri-n-butylamine, 1-N,N-dimethylamino-2-propanol, N,N-dimethyl-2-methoxyethylamine, N-methylmorpholine, and N,N,N',N'-tetramethylhexamethylenediamine. Among these amines, trimethylamine and triethylamine are particularly preferred in view of reaction results, boiling point, solubility, price and other factors. The above-described excellent effects, that are produced by carbonates and/or bicarbonates of monodentate tertiary amines, cannot fully be produced when there are used carbonates and/or bicarbonates of mono- or bidentate tertiary amines having a pKa of less than 7, such as pyridine and dipyridyl, and carbonates and/or bicarbonates of tertiary amines having a pKa of at least 7 but having strong bidentate functionality, such as N,N,N',N'-tetramethyldiaminoethane and N,N-dimethyl-2-aminopropiononitrile.

The carbonate and/or bicarbonate of a monodentate tertiary amine having a pKa of at least 7 exists in the reaction system as an equilibrium mixture of the carbonate and/or bicarbonate ion and the monodentate tertiary amine (as shown by the equilibrium formula below), where the relative amount of the carbonate and/or bicarbonate of the tertiary amine under the reaction conditions depends on the temperature and carbon dioxide partial pressure.

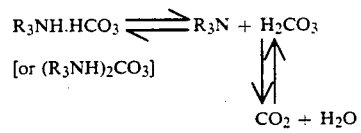

The reaction is therefore generally conducted under such conditions as to assure a carbon dioxide partial pressure of about 1 to 10 atm (absolute partial pressure). In view of reaction results, extraction efficiency, amount of the tertiary amine eluted into the extract layer and like factors, it is preferred that the amount of the carbonate and/or bicarbonate of the tertiary amine used be within the range of 5 to 30% by weight based on the weight of the reaction mixture.

The water to be reacted with butadiene is present in the reaction system as a component in the aqueous sulfolane solution used. The aqueous sulfolane solution not only can withstand long-period continuous use but enables separation of the reaction product by extraction of the reaction mixture. It further has the effect of increasing the reaction rate and selectivity to octa-2,7-dien-1-ol. The water content in the aqueous sulfolane solution is, in view of solubility of butadiene and extraction efficiency of octa-2,7-dien-1-ol, preferably maintained at 70/30 to 30/70 in the weight ratio of water to sulfolane, more preferably at 60/40 to 40/60 on the same basis. A higher water content tends to decrease the reaction rate, while, on the other hand, a lower water content tends to decrease the extraction efficiency of octa-2,7-dien-1-ol and to increase the amounts of sulfolane and catalyst components eluted into the extract.

In the present invention, there are no specific restrictions with respect to the palladium compound to be present in step (1), and for example those catalysts that have been proposed for use in conventional synthesis reaction of octa-2,7-dien-1-ol can be used. Examples of these palladium compounds are palladium acetylacetonate, π-allylpalladium acetate, π-allylpalladium chloride, palladium acetate, palladium carbonate, palladium nitrate, palladium chloride, sodium chloropalladate, bis(benzonitrile) palladium chloride, bis(triphenylphosphine)palladium chloride, bis(triphenylphosphine)palladium acetate, bis(1,5-cyclooctadiene)palladium and bis(π-allyl)palladium. The true active species of a palladium catalyst in the synthesis reaction of octa-2,7-dien-1-ol is a low-valence palladium complex. Where a divalent palladium compound is used as a catalyst, the active species can be formed either by reducing the palladium compound with butadiene that is present in the reaction system, or by reacting a reducing agent with the palladium compound in the same reaction system or in a separate reaction vessel. Examples of the reducing agent for this purpose are alkali metal hydroxides, alkali metal carboxylates, sodium borohydride, zinc dust, magnesium and hydrazine. The palladium compound can be present in the reaction system in any optional amount but, from the standpoint of commercial production, the palladium compound is preferably present in such an amount as to assure the concentration of palladium atom of 0.1 to 50 mg atoms, more preferably 0.5 to 5 mg atoms per liter of the reaction mixture.

The phosphonium salt to be present in step (1) in the present invention is preferably one represented by the following formula (II)

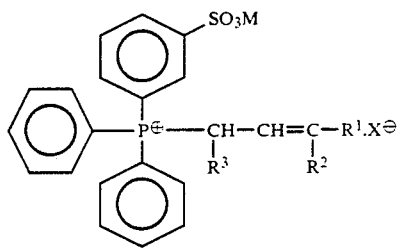
(II)

wherein $R^1$ and $R^2$ each represents a hydrogen atom or a hydrocarbon group having 1 to 12 carbon atoms which may be substituted, $R^3$ represents a hydrogen atom or a hydrocarbon group having 1 to 5 carbon atoms which may be substituted, M represents an alkali metal and X represents a hydroxyl group or a hydrocarbonyloxy group. Examples of the hydrocarbon group having 1 to 12 carbon atoms as represented by $R^1$ or $R^2$ in formula (II) are aliphatic hydrocarbon groups, e.g. alkyl groups such as methyl, ethyl, n-propyl, n-butyl, n-pentyl and n-octyl, and alkenyl groups such as 2-propenyl, 3-butenyl and 4-pentenyl; alicyclic hydrocarbon groups, e.g. cycloalkyl groups such as cyclohexyl; and aromatic hydrocarbon groups, e.g. aryl groups such as phenyl and tolyl, and aralkyl groups such as benzyl. Examples of the hydrocarbon group having 1 to 5 carbon atoms as represented by $R^3$ are aliphatic hydrocarbon groups, e.g. alkyl groups such as methyl, ethyl and propyl; alkenyl groups such as allyl and 4-pentenyl; and the like. Examples of the substituents in the above hydrocarbon groups are di(lower alkyl)amino groups such as dimethylamino group; cyano group; groups represented by the formula —$SO_3M$ or —COOM wherein M represents an alkali metal such as lithium, sodium or potassium). Examples of the alkali metal represented by M are lithium, sodium and potassium.

The amount of the phosphonium salt used is, in view of the rate and selectivity to octa-2,7-dien-1-ol of the reaction, long-time stabilization of the palladium catalyst activity, effect of suppressing elution of the palladium catalyst into the extract in the succeeding extraction step (2) and like factors, generally at least 6 moles per 1 gram atom of palladium, preferably 10 moles on the same basis. While there is no upper limit in the strict sense to the amount of the phosphonium salt used, the phosphonium salt is generally used in an amount of not more than 150 moles per 1 gram atom of palladium, preferably not more than 80 moles on the same basis.

The phosphonium salt represented by formula (II) can readily be obtained by reacting, in the presence of a palladium compound and water containing a carbonate and/or bicarbonate ion, the afore-described phosphine represented by formula (I) with at least one molar equivalent, relative to this phosphine, of an allyl alcohol represented by the formula (III)

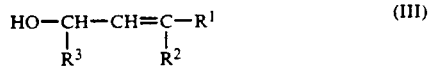
(III)

wherein $R^1$, $R^3$ and $R^3$ are the same as defined before.

The synthesis reaction of octa-2,7-dien-1-ol is generally conducted at a temperature of 50° to 110° C. The reaction vessel may be a per se known apparatus of gas-liquid contact type, such as a stirred-tank reactor, a bubble type reactor or the like.

In step (2) in the present invention, as stated before, octa-2,7-dien-1-ol is separated by extracting with an extracting solvent at least part of the reaction mixture. Extracting solvents usable for this process are those saturated aliphatic hydrocarbons, mono-olefinic hydrocarbons and alicyclic hydrocarbons that have lower boiling points than octa-2,7-dien-1-ol. Examples of these hydrocarbons are saturated hydrocarbons such as n-butane, isobutane, n-pentane, n-hexane, n-heptane, n-octane and isooctane; monoolefinic hydrocarbons such as butene and isobutene and alicyclic hydrocarbons such as cyclohexane, cyclohexene and methylcyclohexane. There can also be used mixtures of hydrocarbons containing butane, butene, isobutene and the like that are contained in C4 fraction used as a butadiene source. Among the above, n-pentane, n-hexane, cyclohexane and methylcyclohexane are particularly preferred. These extracting solvents may be used singly or in combination. In view of extraction efficiency of octa-2,7-dien-1-ol and the amounts of catalyst components and sulfolane eluted into the extract, the extracting solvent is used in a volume ratio of 0.3 to 3 based on the reaction mixture obtained by the synthesis reaction of octa-2,7-dien-1-ol.

It is suitable that the extraction procedure be conducted under an atmosphere of carbon dioxide. The partial pressure of carbon dioxide is preferably higher than 3 absolute pressures and lower than 20 absolute pressures, and more preferably 4 to 16 absolute pressures. If the partial pressure is not higher than 3 absolute pressures, not only the amount of the tertiary amine eluted will increase, but that of palladium catalyst eluted will increase with time; and further the stability of the interface between the catalyst solution and the extract will be worse. On the other hand, a carbon dioxide partial pressure of not lower than 20 absolute pressures means that carbon dioxide is used in an unnecessary and excess amount beyond the amount required for suppressing the elution of palladium catalyst, which is uneconomical. The extraction procedure is preferably conducted at a temperature of 0° to 40° C., more preferably 5° to 30° C. for the purpose of suppressing elution of the palladium catalyst and tertiary amine used. Extraction at a temperature higher than 40° C. will not only increase the amount of the tertiary amine eluted but decompose the product octa-2,7-diene-1-ol in the same catalyst system, thereby decreasing the selectivity; and, further, increase the amount of the palladium catalyst eluted with time accompanied by the decomposition of octa-2,7-dien-1-ol. While the amounts of the palladium catalyst and tertiary amine eluted are inclined to decrease with lowering of extraction temperature, an extraction temperature of lower than 0° C. worsens the separatability of the extraction interface. As the extraction apparatus, there may be used such commercially available one as stirred-tank extractor, RDC extractor or perforated-plate extractor. Upon commercial production, continuous extraction procedure can be conducted by providing a standing tank with sufficient capacity for phase separation.

At least part of the extraction residue containing catalyst components as thus obtained is fed for re-use to the synthesis reaction step (1) of octa-2,7-diene-1-ol. The water-soluble phosphine used in step (4) is fully converted to the phosphonium salt from this washing step (4) through the extraction step (2) to which it has, being incorporated in the aqueous sulfolane solution in step (5), been fed. The water-soluble phosphine is thus not contained in the extraction residue which is fed in step (3) to the synthesis reaction step (1) of octa-2,7-dien-1-ol. Part of the extraction residue may, if desired, be taken out, subjected to catalyst activation treatment, and then circulated to the above synthesis reaction step.

The extract obtained by the extraction step (2) is subjected to the treatment of the afore-described step (4) and then to step (6), to give octa-2,7-dien-1-ol.

According to the present invention, the palladium catalyst used can, nearly perfectly with no increase in the amount of phosphorus compound eluted, be prevented from elution from the reaction system by washing the extract obtained in the extraction step with an aqueous sulfolane solution containing a water-soluble phosphine. Furthermore, the palladium catalyst thus recovered maintains its activity, whereby it is required to add only a trace amount of new catalyst for making up the amount eluted. Addition of dimethylglyoxime to the washed extract can minimize various troubles generating upon separation by distillation of octa-2,7-dien-1-ol as caused by a trace amount of the palladium catalyst contained in the extract.

Further according to the present invention, the recovery rates of tertiary amine such as triethylamine and of sulfolane increase, and intermixing of byproducts into the reaction system is minimized to keep their steady-state concentration at a minimum. The palladium catalyst used can therefore maintain high activity.

Hydrogenation of octa-2,7-dien-1-ol gives n-octanol, which is useful as a starting material for plasticizers such as dioctyl phthalate. Hydrogenation of the product obtained by subjecting octa-2,7-dien-1-ol to oxo reaction gives 1,9-nonanediol, which is useful as a starting material for producing polyesters having high resistance to hydrolysis.

Other features of the invention will become apparent in the course of the following descriptions of exemplary embodiments which are given for illustration of the invention and are not intended to be limiting thereof.

EXAMPLES

EXAMPLE 1

Continuous reaction was conducted using the following apparatuses under the conditions described later, and the reaction results at steady state were studied.

Reactor

A stainless-steel pressure-proof reactor equipped with a temperature controller, stirrer, constant-rate feed pump of butadiene, catalyst solution feed pump, carbon dioxide inlet, pressure-control valve and level gauge. The reaction mixture is fed to the extractor via a pressure reducing valve.

Extractor

A mixer-settler type extractor equipped with a pressure reducing valve, pressure-control valve, thermometer, stirrer, extracting solvent feed pump, supplementary liquid feed pump, level gauge and interface level gauge. The extraction residue catalyst solution is fed at a constant rate by a catalyst solution feed pump to the reactor via a catalyst reservoir. The extract is fed at a constant rate by an extract feed pump to the apparatus for washing extract with aqueous sulfolane solution.

Apparatus for Washing Extract with Aqueous Sulfolane Solution

An apparatus equipped with an extract feed pump, aqueous sulfolane solution feed pump, static mixer and standing tank. The lower layer of aqueous sulfolane solution is fed by a supplementary liquid feed pump to the catalyst preparation tank and the extractor. The upper layer of the washed extract layer is fed to the butadiene recovery column via a pressure reducing valve.

Distillation Apparatus

A distillation column equipped with a butadiene recovery column (recovers butadiene and carbon dioxide), extracting solvent recovery column (recovers extracting solvent and tertiary amine), a thin-film evaporator (recovers eluted palladium catalyst and eluted phosphorus compound and cuts high boiling substances), a column for cutting low boiling substances and a purifying column (purifies octa-2,7-dien-1-ol).

Sulfolane Recovery Apparatus

A recovery apparatus equipped with a water feed pump, a static mixer and a standing tank. The lower layer is fed by aqueous sulfolane solution feed pump to the apparatus for washing extract with aqueous sulfolane solution.

Attached Apparatuses

Various tanks and a catalyst preparation tank.

Operating Conditions and Operation Results

The reaction conditions were: temperature: 70° C., pressure: 14 kg/cm$^2$G (applied by carbon dioxide) and residence time of the reaction mixture: 1.0 hour. The composition of the reaction mixture (homogeneous solution) in the reactor at steady state was maintained at: 30% by weight of sulfolane, 27.5% by weight of water, 9.6% by weight of triethylamine, 1.1 mg atoms/l (as palladium atom) of palladium catalyst (formed from palladium acetate), 41 mmoles/l of a phosphonium salt represented by formula

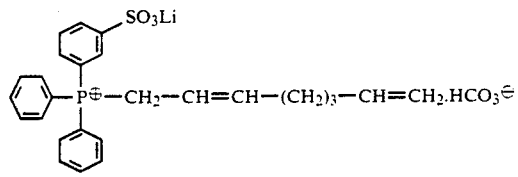

1.2 moles/l of butadiene and 0.9 mole/l of octa-2,7-dien-1-ol.

The above reaction mixture was continuously extracted at 20° C. with an extracting solvent (n-hexane containing a trace amount of triethylamine) in a volume ratio of reaction mixture/extracting solvent of 0.8 under a carbon dioxide pressure of 6 absolute pressures. The product, butadiene, triethylamine and sulfolane in the extract were analyzed by gas chromatography, the palladium catalyst by atomic absorption analysis and the phosphorus compound by calorimetry. The concentration of octa-2,7-dien-1-ol in the extract was found to be 10% by weight, and the amounts of the solvent and the catalysts eluted into the extract were 1.2 ppm for the palladium catalyst (as palladium atom), 3.6 ppm for the phosphorus compound (as phosphorus atom), 1.0% by weight for sulfolane, 0.40% by weight for triethylamine and 0.15% by weight for water.

To 1,000 parts by weight of the extract was added an aqueous sulfolane solution containing 11 parts by weight of sulfolane, 1.5 parts by weight of C9 lactone and 15 parts by weight of water (having dissolved lithium diphenylphosphino-benzene-m-sulfonate in an amount of 1.5 times mole of the palladium catalyst in the extract), and the mixture was stirred with a static mixer at 20° C. under 6 absolute pressures (applied by carbon dioxide) and then separated in a standing tank. Analysis of the upper layer revealed that the concentration of octa-2,7-dien-1-ol was 10% by weight, showing no change, and that the amounts of the solvents and the catalysts eluted were 0.06 ppm for the palladium catalyst (as palladium atom), 0.7 ppm for the phosphorus compound (as phosphorus atom), 1.05% by weight for sulfolane, 0.12% by weight for triethylamine and 0.15% by weight for water. This means that 95% of the palladium catalyst, 80% of the phosphorus compound and 70% of triethylamine had been recovered into the lower layer. The lower layer containing 11 parts by weight of sulfolane, 15 parts by weight of water and 0.2 part by weight of C9 lactone was continuously fed to the extractor. The concentration of C9 lactone in the catalyst solution was 0.3% by weight. High-performance liquid chromatography on the catalyst solution could not find the presence of lithium diphenylphosphinobenzene-m-sulfonate.

The upper layer was fed to the distillation apparatus, where butadiene, carbon dioxide and triethylamine were nearly quantitatively recovered and octa-2,7-dien-1-ol with a purity of 99.9% was obtained.

To 16 parts by weight of the waste comprising 11.5 parts by weight of sulfolane and 3 parts by weight of C9 lactone were added 16 parts by weight of hexane and 15 parts by weight of water, and the mixture was stirred well with a static mixer and then kept standing still. An aqueous sulfolane solution containing 11 parts by weight of sulfolane and 1.5 parts by weight of C9 lactone was obtained as the lower layer. This result shows that the recovery rate of sulfolane was 96%. The aqueous sulfolane solution thus obtained was fed at a constant rate to the apparatus for washing extract.

In the catalyst preparation tank, the palladium catalyst and the phosphonium salt were, in amounts corresponding to those lost outward, dissolved in the aqueous sulfolane solution, and the obtained solution was fed to the reactor to maintain the concentrations of the palladium catalyst and the phosphonium salt in the reaction mixture nearly constant. For the purpose of fine-control of the concentrations of sulfolane and water in the reaction mixture, fresh aqueous sulfolane solution and water were appropriately, from time to time, fed to the extractor. The concentration of triethylamine in the reaction mixture was fine-controlled by, as necessary, feeding triethylamine to the extracting solvent.

A continuous running was conducted with the above procedures for 21 days, during which operation was very stable and showed a constant reaction result.

Comparative Example 1

Example 1 was repeated except that sulfolane was recovered by the following method, the washing of the extract with the aqueous sulfolane solution recovered in the distillation was omitted and the recovered aqueous sulfolane solution was directly fed to the extractor, under the same conditions of reaction, extraction and distillation, to conduct a 7 day continuous run.

In recovering sulfolane, 13 parts by weight of water was added to 16 parts by weight of the waste containing 10.9 parts by weight of sulfolane and 4 parts by weight of C9 lactone and the mixture was stirred well with a static mixer and allowed to stand still. An aqueous sulfolane solution containing 10 parts by weight of sulfolane and 1.4 parts by weight of C9 lactone was obtained as the lower layer. This shows that the recovery rate of sulfolane was 92%.

As a result, the concentration of C9 lactone in the catalyst solution increased to 1.2% by weight and that of octa-2,7-dien-1-ol in the extract decreased to 9.2% by weight. The amounts of solvents and catalysts eluted into the extract were 1.7 ppm for the palladium catalyst (as palladium atom), 3.9 ppm for the phosphorus compound (as phosphorus atom), 1.0% by weight for sulfolane, 0.4% by weight for triethylamine and 0.14% by weight for water.

The above results show that omission of the washing of extract with an aqueous sulfolane solution causes the productivity to decrease and the amount of palladium catalyst elution to increase.

EXAMPLE 2

Recovery of palladium catalyst from an extract containing it was studied by using the extract obtained in Example 1. A 1-liter pressure-proof glass autoclave equipped with an electromagnetic stirrer and substituted with carbon dioxide gas was charged by gas pressure with 700 ml of the extract obtained in Example 1 (460 g, containing 0.56 mg of palladium atom and 1.69 mg of phosphorus atom) and the contents were placed under a carbon dioxide pressure of 5 kg/cm$^2$G at 20° C. While the contents were stirred at 1000 rpm, the autoclave was fed with water or aqueous sulfolane solutions in amounts as shown in Table 1 and the contents were stirred for 30 minutes. A water-soluble phosphorus compound was dissolved in the aqueous sulfolane solutions and added. Each of the mixture thus obtained was allowed to stand still for 10 minutes. Then, the lower layer was withdrawn and thereafter the upper layer was withdrawn. The palladium catalyst and phosphorus compound in the upper and lower layers were analyzed by atomic absorption analysis and calorimetry, respectively. The results are shown in Table 1.

TABLE 1

| Test No. | Aqueous sulfolane solution | | Addition of P[1] mole ratio of P/Pd | Recovery rate into lower layer | |
|---|---|---|---|---|---|
| | sulfolane (g) | water (g) | | Pd | P |
| 1 | 0 | 7 | 0 | 33 | 30 |
| 2 | 0 | 14 | 0 | 26 | 29 |
| 3 | 5 | 7 | 0 | 38 | 72 |
| 4 | 5 | 7 | 1.5 | 94 | 74 |
| 5 | 5 | 7 | 3 | 98 | 68 |
| 6 | 3.6 | 5 | 2 | 97 | 70 |

P[1] means lithium diphenylphosphinobenzene-m-sulfonate

It is clear from Table 1 that where an aqueous sulfolane solution is used, the recovery rate of the phosphorus compound eluted increases, with that of the palladium catalyst showing no change; and that where a water-soluble phosphorus compound is added, the palladium catalyst is recovered nearly quantitatively, while the recovery rate of the phosphorus compound eluted remains constant.

EXAMPLE 3

Recovery of sulfolane from a waste in step (6) was studied.

To 100 g of the waste with a composition of 64% by weight of sulfolane, 19% by weight of C9 lactone and 12% by weight of dioctadienyl ether, were added hexane and water in amounts as shown in Table 2 and the contents were stirred at room temperature and allowed to stand still. Recovery rates into the lower layer are shown in Table 2.

TABLE 2

| Test No. | Hexane (g) | Water (g) | Recovery rate into lower layer | | |
|---|---|---|---|---|---|
| | | | sulfolane | C9 lactone | dioctadienyl ether |
| 1 | 17 | 0 | 98 | 90 | 25 |
| 2 | 67 | 0 | 98 | 89 | 9.4 |
| 3 | 308 | 0 | 97 | 75 | 2.3 |
| 4 | 0 | 100 | 90 | 36 | 1.4 |
| 5 | 0 | 200 | 93 | 36 | 0 |
| 6 | 67 | 100 | 94 | 47 | 0 |
| 7 | 302 | 100 | 99 | 48 | 0 |

It is clear from Table 2 that while the recovery rate of sulfolane is low when water is used alone, sulfolane is recovered nearly quantitatively when hexane is used singly or in combination with water. In this case, C9 lactone is also eluted into the lower layers, it is re-extracted into hexane layer in step (4).

EXAMPLE 4

To the extract obtained in Example 2, compounds as shown in Table 3 were separately added under an atmosphere of nitrogen, and each mixture was heated at 150° C. for 3 hours, where hexane distilled out and the mixture was condensed to about 7 times and palladium metal was observed to be precipitated. The condensed solutions were filtered and quantitatively analyzed for the palladium catalyst dissolved therein by atomic absorption analysis.

TABLE 3

| Additive | additive/Pd (mole ratio) | remaining Pd dissolved (%) |
|---|---|---|
| None | 0 | 29 |
| Dimethylglyoxime | 21 | 92 |
| Dimethylglyoxime | 70 | 100 |
| Dipyridyl | 70 | 55 |
| 8-hydroxyquinoline | 20 | 37 |

It is clear from Table 3 that the presence of dimethylglyoxime in the extract prevents the palladium catalyst that has been eluted thereinto from precipitating as palladium metal.

Comparative Example 2

The reaction conditions were: temperature: 70° C., pressure: 14 kg/cm$^2$G (applied by carbon dioxide) and residence time of the reaction mixture: 1.0 hour. The composition of the reaction mixture (homogeneous solution) in the reactor at steady state was maintained at: 29% by weight of sulfolane, 28.5% by weight of water, 9.8% by weight of triethylamine, 1.3 mg atoms/l (as palladium atom) of palladium catalyst (formed from palladium acetate), 39 mmoles/l of a phosphonium salt represented by formula

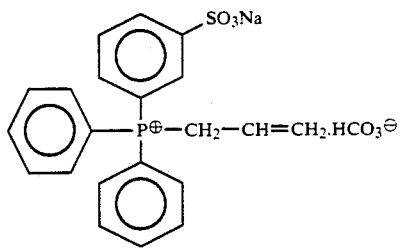

1.0 mole/l of butadiene and 0.9 mole/l of octa-2,7-dien-1-ol.

The above reaction mixture was continuously extracted at 20° C. with an extracting solvent (n-hexane containing a trace amount of triethylamine) in a volume ratio of reaction mixture/extracting solvent of 0.6 under a carbon dioxide pressure of 6 absolute pressure. The product, butadiene, triethylamine and sulfolane in the extract were analyzed by gas chromatography, the palladium catalyst by atomic absorption analysis and the phosphorus compound by calorimetry. The concentration of octa-2,7-dien-1-ol in the extract was found to be 11.2% by weight, and the amounts of the solvent and the catalysts eluted into the extract were 1.5 ppm for the palladium catalyst (as palladium atom), 4.3 ppm for the phosphorus compound (as phosphorus atom), 1.2% by weight for sulfolane, 0.48% by weight for triethylamine and 0.18% by weight for water.

To 1,000 parts by weight of the extract were added a sulfolane solution containing 12.3 parts by weight of sulfolane and 2.8 parts by weight of C9 lactone and 16 parts by weight of water, and the mixture was stirred with a static mixer at 20° C. under 6 absolute pressures (applied by carbon dioxide) and then separated in a standing tank. Analysis of the upper layer revealed that the concentration of octa-2,7-dien-1-ol was 11.2% by weight, showing no change, and that the amounts of the solvents and the catalysts eluted were 0.97 ppm for the palladium catalyst (as palladium atom), 0.9 ppm for the phosphorus compound (as phosphorus atom), 1.25% by weight for sulfolane, 0.12% by weight for triethylamine and 0.16% by weight for water. This means that 35% of the palladium catalyst, 80% of the phosphorus compound and 75% of triethylamine had been recovered into the lower layer. The lower layer containing 12 parts by weight of sulfolane, 16 parts by weight of water and 0.3 parts by weight of C9 lactone was continuously fed to the extractor. The concentration of C9 lactone in the catalyst solution was 0.3% by weight.

EXAMPLE 5

The reaction conditions were: temperature: 70° C., pressure: 14 kg/cm$^2$G (applied by carbon dioxide) and residence time of the reaction mixture: 1.2 hour. The composition of the reaction mixture (homogeneous solution) in the reactor at steady state was maintained at: 35% by weight of sulfolane, 25% by weight of water, 5.2% by weight of trimethylamine, 1.2 mg atoms/l (as palladium atom) of palladium catalyst (formed from palladium acetate), 36 mmoles/l of a phosphonium salt represented by formula

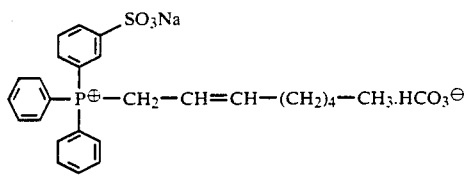

1.2 moles/l of butadiene and 1.0 mole/l of octa-2,7-dien-1-ol.

The above reaction mixture was continuously extracted at 20° C. with an extracting solvent (n-hexane containing a trace amount of trimethylamine) in a volume ratio of reaction mixture/extracting solvent of 0.8 under a carbon dioxide pressure of 6 absolute pressures. The product, butadiene, trimethylamine and sulfolane in the extract were analysed by gas chromatography, the palladium catalyst by atomic absorption analysis and the phosphorus compound by calorimetry. The concentration of octa-2,7-dien-1-ol in the extract was found to be 9.3% by weight, and the amounts of the solvent and the catalysts eluted into the extract were 1.5 ppm for the palladium catalyst (as palladium atom), 3.0 ppm for the phosphorus compound (as phosphorus atom), 1.3% by weight for sulfolane, 0.10% by weight for trimethylamine and 0.15% by weight for water.

To 1,000 parts by weight of the extract was added an aqueous sulfolane solution containing 13 parts by weight of sulfolane, 1.5 parts by weight of C9 lactone and 15 parts by weight of water (having dissolved sodium diphenylphosphinobenzene-m-sulfonate in an amount of 1.5 times mole of the palladium catalyst in the extract), and the mixture was stirred with a static mixer at 20° C. under 6 absolute pressures (applied by carbon dioxide) and then separated in a standing tank. Analysis of the upper layer revealed that the concentration of octa-2,7-dien-1-ol was 9.3% by weight, showing no change, and that the amounts of the solvents and the catalysts eluted were 0.10 ppm for the palladium catalyst (as palladium atom), 0.4 ppm for the phosphorus compound (as phosphorus atom), 1.2% by weight for sulfolane, 0.05% by weight for trimethylamine and 0.15% by weight for water. This means that 93% of the palladium catalyst, 87% of the phosphorus compound and 50% of trimethylamine had been recovered into the lower layer. The lower layer containing 13 parts by weight of sulfolane, 15 parts by weight of water and 0.2 part by weight of C9 lactone was continuously fed to the extractor. The concentration of C9 lactone in the catalyst solution was 0.3% by weight. High-performance liquid chromatography on the catalyst solution could not find the presence of sodium diphenylphosphinobenzene-m-sulfonate.

The upper layer was fed to the distillation apparatus, where butadiene, carbon dioxide and trimethylamine were nearly quantitatively recovered and octa-2,7-dien-1-ol with a purity of 99.9% was obtained.

To 20 parts by weight of the waste comprising 14 parts by weight of sulfolane and 4 parts by weight of C9 lactone were added 20 parts by weight of hexane and 15 parts by weight of water, and the mixture was stirred well with a static mixer and then kept standing still. An aqueous sulfolane solution containing 13 parts by weight of sulfolane and 1.5 parts by weight of C9 lactone was obtained as the lower layer. This result shows that the recovery rate of sulfolane was 93%. The aqueous sulfolane solution thus obtained was fed at a constant rate to the apparatus for washing extract.

In the catalyst preparation tank, the palladium catalyst and the phosphonium salt were, in amounts corresponding to those lost outward, dissolved in the aqueous sulfolane solution, and the obtained solution was fed to the reactor to maintain the concentrations of the palladium catalyst and the phosphonium salt in the reaction mixture nearly constant. For the purpose of fine-control of the concentrations of sulfolane and water in the reaction mixture, fresh aqueous sulfolane solution and water were appropriately, from time to time, fed to the extractor. The concentration of trimethylamine in the reaction mixture was fine-controlled by, as necessary, feeding trimethylamine to the extracting solvent.

A continuous running was conducted with the above procedures for 7 days, during which operation was very stable and showed a constant reaction result.

EXAMPLE 6

The reaction conditions were: temperature: 70° C., pressure: 14 kg/cm$^2$G (applied by carbon dioxide) and residence time of the reaction mixture: 1.0 hour. The composition of the reaction mixture (homogeneous solution) in the reactor at steady state was maintained at: 31% by weight of sulfolane, 27% by weight of water, 9.8% by weight of triethylamine, 1.1 mg atoms/l (as palladium atom) of palladium catalyst (formed from palladium acetate), 41 mmoles/l of a phosphonium salt represented by formula

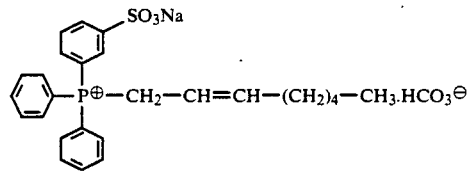

1.2 moles/l of butadiene and 0.9 mole/l of octa-2,7-dien-1-ol.

The above reaction mixture was continuously extracted at 20° C. with an extracting solvent (cyclohexane containing a trace amount of triethylamine) in a volume ratio of reaction mixture/extracting solvent of 0.8 under a carbon dioxide pressure of 6 absolute pressures. The product, butadiene, triethylamine and sulfolane in the extract were analyzed by gas chromatography, the palladium catalyst by atomic absorption analysis and the phosphorus compound by calorimetry. The concentration of octa-2,7-dien-1-ol in the extract was found to be 9.5% by weight, and the amounts of the solvent and the catalysts eluted into the extract were 3.5 ppm for the palladium catalyst (as palladium atom), 4.7 ppm for the phosphorus compound (as phosphorus atom), 1.8% by weight for sulfolane, 0.6% by weight for triethylamine and 0.2% by weight for water.

To 1,000 parts by weight of the extract was added an aqueous sulfolane solution containing 18 parts by weight of sulfolane, 1.4 parts by weight of C9 lactone and 15 parts by weight of water (having dissolved sodium diphenylphosphino-benzene-m-sulfonate in an amount of 1.5 times mole of the palladium catalyst in the extract), and the mixture was stirred with a static mixer at 20° C. under 6 absolute pressures (applied by carbon dioxide) and then separated in a standing tank. Analysis of the upper layer revealed that the concentration of octa-2,7-dien-1-ol was 9.5% by weight, showing no change, and that the amounts of the solvents and the catalysts eluted were 0.35 ppm for the palladium catalyst (as palladium atom), 1.4 ppm for the phosphorus compound (as phosphorus atom), 1.83% by weight for sulfolane, 0.21% by weight for triethylamine and 0.15% by weight for water. This means that 90% of the palladium catalyst, 70% of the phosphorus compound and 65% of triethylamine had been recovered into the lower layer. The lower layer containing 18 parts by weight of sulfolane, 15 parts by weight of water and 0.2 part by weight of C9 lactone was continuously fed to the extractor. The concentration of C9 lactone in the catalyst solution was 0.4% by weight. High-performance liquid chromatography on the catalyst solution could not find the presence of sodium diphenylphosphinobenzene-m-sulfonate.

The upper layer was fed to the distillation apparatus, where butadiene, carbon dioxide and triethylamine were nearly quantitatively recovered and octa-2,7-dien-1-ol with a purity of 99.9% was obtained.

To 25 parts by weight of the waste comprising 19 parts by weight of sulfolane and 3 parts by weight of C9 lactone were added 25 parts by weight of hexane and 15 parts by weight of water, and the mixture was stirred well with a static mixer and then kept standing still. An aqueous sulfolane solution containing 18 parts by weight of sulfolane and 1.5 parts by weight of C9 lactone was obtained as the lower layer. This result shows that the recovery rate of sulfolane was 95%. The aqueous sulfolane solution thus obtained was fed at a constant rate to the apparatus for washing extract.

In the catalyst preparation tank, the palladium catalyst and the phosphonium salt were, in amounts corresponding to those lost outward, dissolved in the aqueous sulfolane solution, and the obtained solution was fed to the reactor to maintain the concentrations of the palladium catalyst and the phosphonium salt in the reaction mixture nearly constant. For the purpose of fine-control of the concentrations of sulfolane and water in the reaction mixture, fresh aqueous sulfolane solution and water were appropriately, from time to time, fed to the extractor. The concentration of triethylamine in the reaction mixture was fine-controlled by, as necessary, feeding triethylamine to the extracting solvent.

A continuous running was conducted with the above procedures for 6 days, during which operation was very stable and showed a constant reaction result.

Obviously, numerous modifications and variations of the present invention are possible in light of the above teachings. It is therefore to be understood that within the scope of the appended claims, the invention may be practiced otherwise than as specifically described herein.

We claim:

1. A process for producing octa-2,7-dien-1-ol, which comprises:
   (1) reacting butadiene with water in an aqueous sulfolane solution containing a carbonate and/or bicarbonate of an monodentate tertiary amine having a basicity constant (pKa) of at least 7 in the presence of a palladium compound and at least 6 moles per gram atom of palladium of a phosphonium salt of the formula:

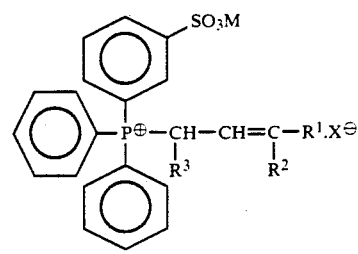

II wherein $R^1$ and $R^2$ each represents a hydrogen atom or a hydrocarbon group having 1 to 12 carbon atoms which may be substituted by di(lower alkyl) amino, cyano, or groups represented by the formula $SO_3M$ or $—COOM$ wherein M represents an alkali metal, $R^3$ represents a hydrogen atom or a hydrocarbon group having 1 to 5 carbon atoms which may be substituted by di(lower alkyl) amino, cyano, or groups represented by the formula $SO_3M$ or $—COOM$ wherein M represents an alkali metal and X represents a hydroxyl group or a hydrocarbonyloxy group, while maintaining the mole ratio of butadiene to octa-2,7-dien-1-ol at at least 0.6, to synthesize octa-2,7-dien-1-ol;

(2) separating octa-2,7-dien-1-ol by extracting at least part of the reaction mixture obtained in step (1) with a saturated aliphatic hydrocarbon, a monoolefinic hydrocarbon or an alicyclic hydrocarbon;

(3) feeding at least part of the extraction residue containing the catalyst components as obtained in step (2) to the synthesis reaction step (1) of octa-2,7-dien-1-ol;

(4) washing the extract containing octa-2,7-dien-1-ol as obtained in step (2) with an aqueous sulfolane solution in the presence of a water-soluble phosphine and separating the mixture into the aqueous sulfolane solution layer and the washed extract layer;

(5) feeding at least part of the aqueous sulfolane solution layer obtained in step (4) to the extraction step (2); and (6) distilling the washed extract layer obtained in step (4), to obtain octa-2,7-dien-1-ol.

2. The process according to claim 1, wherein said tertiary amine is trimethylamine or triethylamine.

3. The process according to claim 1 or claim 2, wherein the amount of said phosphonium salt is from 6 to 150 moles per gram atom of palladium.

4. The process according to claim 1, wherein the amount of said water-soluble phosphine is at least 1 equivalent based on the gram equivalent of the palladium atom contained in the extract containing octa-2,7-dien-1-ol.

5. The process according to claim 1, said process comprising recovering sulfolane by adding hexane to the waste obtained in step (6) or the liquid obtained by evaporation thereof.

6. The process according to claim 1, said process comprising recovering sulfolane by adding water or a mixture of water and hexane to the waste obtained in step (6) or the liquid obtained by evaporation thereof.

7. The process according to claim 1, said process comprising using the sulfolane recovered in the process of claim 5 or claim 6 as the aqueous sulfolane solution in step (4).

8. The process according to claim 1, said process comprising adding to the washed extract layer obtained in step (4) dimethylglyoxime in a mole ratio to the palladium atom present in said extract layer of at least 10.

9. A process for producing octa-2,7-dien-1-ol, which comprises:

(1) reacting butadiene with water in an aqueous sulfolane solution containing a carbonate and/or bicarbonate of an monodentate tertiary amine having a basicity constant (pKa) of at least 7 in the presence of a palladium compound and an amount of a phosphonium salt of the formula:

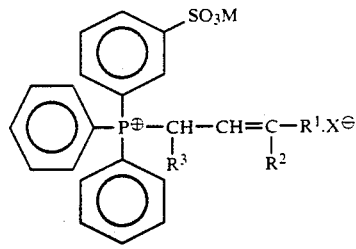

sufficient to selectively produce octa-2,7-dien-1-ol, provide long-term stabilization of said palladium compound, and allow for efficient recovery of said palladium and said phosphonium salt at later stages of the process, wherein $R^1$ and $R^2$ each represents a hydrogen atom or a hydrocarbon group having 1 to 12 carbon atoms which may be substituted by di(lower alkyl) amino, cyano, or groups represented by the formula $SO_3M$ or —COOM wherein M represents an alkali metal, $R^3$ represents a hydrogen atom or a hydrocarbon group having 1 to 5 carbon atoms which may be substituted by di(lower alkyl) amino, cyano, or groups represented by the formula $SO_3M$ or —COOM wherein M represents an alkali metal and X represents a hydroxyl group or a hydrocarbonyloxy group, while maintaining the mole ratio of butadiene to octa-2,7-dien-1-ol at least 0.6, to synthesize octa-2,7-dien-1-ol;

(2) separating octa-2,7-dien-1-ol by extracting at least part of the reaction mixture obtained in step (1) with a saturated aliphatic hydrocarbon, a monoolefinic hydrocarbon or an alicyclic hydrocarbon;

(3) feeding at least part of the extraction residue containing the catalyst components as obtained in step (2) to the synthesis reaction step (1) of octa-2,7-dien-1-ol;

(4) washing the extract containing octa-2,7-dien-1-ol as obtained in step (2) with an aqueous sulfolane solution in the presence of a water-soluble phosphine and separating the mixture into the aqueous sulfolane solution layer and the washed extract layer;

(5) feeding at least part of the aqueous sulfolane solution layer obtained in step (4) to the extraction step (2); and (6) distilling the washed extract layer obtained in step (4), to obtain octa-2,7-dien-1-ol.

* * * * *